United States Patent
Allen, IV

(10) Patent No.: US 11,304,716 B2
(45) Date of Patent: Apr. 19, 2022

(54) SURGICAL INSTRUMENTS INCLUDING TOUCH-SENSING ACTUATION

(71) Applicant: COVIDIEN LP, Mansfield, MA (US)

(72) Inventor: James D. Allen, IV, Broomfield, CO (US)

(73) Assignee: Covidien LP, Mansfield, MA (US)

( * ) Notice: Subject to any disclaimer, the term of this patent is extended or adjusted under 35 U.S.C. 154(b) by 904 days.

(21) Appl. No.: 15/240,257

(22) Filed: Aug. 18, 2016

(65) Prior Publication Data

US 2017/0172594 A1 Jun. 22, 2017

Related U.S. Application Data

(60) Provisional application No. 62/268,222, filed on Dec. 16, 2015.

(51) Int. Cl.

| *A61B 18/14* | (2006.01) |
| *A61B 17/295* | (2006.01) |
| *A61B 17/00* | (2006.01) |
| *A61B 90/00* | (2016.01) |
| *A61B 18/00* | (2006.01) |

(52) U.S. Cl.
CPC ........ *A61B 17/295* (2013.01); *A61B 18/1445* (2013.01); *A61B 2017/00017* (2013.01); *A61B 2017/00207* (2013.01); *A61B 2017/00367* (2013.01); *A61B 2017/00398* (2013.01); *A61B 2018/00702* (2013.01); *A61B 2018/1455* (2013.01); *A61B 2090/064* (2016.02); *A61B 2090/065* (2016.02)

(58) Field of Classification Search
CPC .......... A61B 2017/00367; A61B 2017/00207; A61B 2017/00199; A61B 2017/00017; A61B 2090/064; A61B 2090/065; A61B 17/295; A61B 18/1445; A61B 2017/00398; A61B 2018/00702; A61B 2018/1455

See application file for complete search history.

(56) References Cited

U.S. PATENT DOCUMENTS

| 8,127,046 B2 | 2/2012 | Grant et al. |
| 8,239,784 B2 | 8/2012 | Hotelling et al. |
| 8,388,541 B2 | 3/2013 | Messerly et al. |
| 8,801,710 B2 | 8/2014 | Ullrich et al. |
| 8,970,503 B2 | 3/2015 | Christie et al. |

(Continued)

FOREIGN PATENT DOCUMENTS

CN 202563449 U 11/2012

*Primary Examiner* — Eun Hwa Kim
*Assistant Examiner* — Adam Z Minchella
(74) *Attorney, Agent, or Firm* — Carter, DeLuca & Farrell LLP

(57) ABSTRACT

A surgical instrument includes a housing including a touch sensor having a sensor surface disposed thereon. The touch sensor is configured to sense an actuation pattern input on the sensor surface. A shaft extends distally from the housing and includes an end effector disposed at a distal end thereof. An actuation assembly is disposed within the housing and operably coupled to the end effector. A control module is operably coupled between the sensor surface and the actuation assembly. The control module is configured, in response to input of an actuation pattern on the sensor surface, to actuate the actuation assembly such that a function is performed at the end effector.

19 Claims, 7 Drawing Sheets

(56) References Cited

U.S. PATENT DOCUMENTS

| | | |
|---|---|---|
| 9,072,479 B2 | 7/2015 | Wood |
| 9,098,142 B2 | 8/2015 | Westerman et al. |
| 2006/0101694 A1* | 5/2006 | Matteson ................ F41A 17/06 42/69.01 |
| 2007/0055228 A1* | 3/2007 | Berg .............. A61B 17/320092 606/41 |
| 2011/0213225 A1 | 9/2011 | Bernstein et al. |
| 2013/0072951 A1 | 3/2013 | Trezza, II et al. |
| 2013/0096539 A1 | 4/2013 | Wood et al. |
| 2013/0144188 A1 | 6/2013 | Fiebig et al. |
| 2013/0165854 A1* | 6/2013 | Sandhu .................. A61B 34/20 604/95.01 |
| 2013/0172906 A1* | 7/2013 | Olson .................... A61B 34/74 606/130 |
| 2014/0306877 A1 | 10/2014 | Katz et al. |
| 2015/0141988 A1 | 5/2015 | Palmer et al. |
| 2015/0272572 A1* | 10/2015 | Overmyer ........ A61B 17/07207 227/177.1 |

\* cited by examiner

SURGICAL INSTRUMENTS INCLUDING TOUCH-SENSING ACTUATION

CROSS REFERENCE TO RELATED APPLICATION

The present application claims the benefit of and priority to U.S. Provisional Application Ser. No. 62/268,222, filed on Dec. 16, 2015, the entire contents of which are incorporated herein by reference.

BACKGROUND

Technical Field

The present disclosure relates to surgical instruments and, more particularly, to surgical instruments including touch-sensing actuation of the functional components and/or features thereof.

Background of Related Art

Many surgical instruments include one or more movable handles, levers, actuators, triggers, etc. for actuating one or more functional components and/or features of the surgical instrument. For example, a surgical forceps may include a movable handle that is selectively compressible relative to a stationary handle for moving first and second jaw members between spaced-apart and approximated positions for grasping tissue therebetween. Such a forceps may further include a trigger for selectively deploying a knife between the jaw members to cut tissue grasped therebetween, an activation button for initiating the supply of energy to the first and second jaw members, and/or a rotation knob for enabling rotation of the jaw members.

As can be appreciated, as functional components and/or features are added to surgical instruments, additional deployment structures and/or multi-purpose deployment structures are required. In determining where to position these additional deployment structures and/or multi-purpose deployment structures, ergonomics, safety, spatial constraints, and functional constraints must be considered in order to ensure the resulting surgical instrument is relatively easy to use, comfortable, and not overly stressful or fatigue-causing.

SUMMARY

As used herein, the term "distal" refers to the portion that is being described which is further from a user, while the term "proximal" refers to the portion that is being described which is closer to a user. Further, to the extent consistent, any of the aspects described herein may be used in conjunction with any or all of the other aspects described herein.

Provided in accordance with aspects of the present disclosure is a surgical instrument including a housing, a shaft extending distally from the housing, an end effector disposed at a distal end of the shaft, an actuation assembly disposed within the housing, and a control module. The housing includes a touch sensor having a sensor surface disposed thereon. The touch sensor is configured to sense an actuation pattern input on the sensor surface. The control module is operably coupled between the sensor surface and the actuation assembly and is configured, in response to input of an actuation pattern on the sensor surface, to actuate the actuation assembly such that a function is performed at the end effector.

In an aspect of the present disclosure, the end effector includes first and second jaw members and the function includes moving the first and second jaw members from a spaced-apart position to an approximated position to grasp tissue therebetween. In such aspects, the actuation pattern may be configured to mimic actuation of a movable handle.

In another aspect of the present disclosure, a knife is slidably disposed within the shaft and the function includes deploying the knife relative to the end effector to cut tissue. In such aspects, the actuation pattern may be configured to mimic actuation of a trigger.

In yet another aspect of the present disclosure, the function includes rotating the end effector. In such aspects, the actuation pattern may be configured to mimic actuation of a rotation wheel.

In still another aspect of the present disclosure, the function includes supplying energy from the end effector to tissue to treat tissue. In such aspects, the actuation pattern may be configured to mimic depression of an activation button.

In still yet another aspect of the present disclosure, the control module is subject to one or more override protocols. The override protocol(s) inhibit actuation of the actuation assembly even if the actuation pattern is input on the sensor surface.

In another aspect of the present disclosure, the actuation pattern is user-programmable. More specifically, the actuation pattern may be selected from a plurality of pre-set actuation patterns or may be user-defined.

In still another aspect of the present disclosure, the sensor surface occupies a portion of a surface area of the housing that is less than the entire surface area of the housing. Alternatively, the sensor surface may occupy the entire surface area of the housing.

Another surgical instrument provided in accordance with aspects of the present disclosure includes a housing, a shaft extending distally from the housing, an end effector disposed at a distal end of the shaft, first and second actuation assemblies disposed within the housing and operably coupled to the end effector, and a control module. The housing includes one or more touch sensors each having one or more sensor surfaces disposed thereon. The one or more touch sensors are configured to sense a plurality of different actuation patterns input on the sensor surface(s) including a first actuation pattern and a second actuation pattern. A plurality of different functions including a first function and a second function are capable of being performed at the end effector. The control module is operably coupled between the sensor surface(s) and the first and second actuation assemblies and is configured, in response to input of the first actuation pattern on the sensor surface(s), to actuate the first actuation assembly such that the first function is performed at the end effector. The control module is further configured, in response to input of the second actuation pattern on the sensor surface(s), to actuate the second actuation assembly such that the second function is performed at the end effector.

In an aspect of the present disclosure, the end effector includes first and second jaw members. In such aspects, the first function includes moving the first and second jaw members from a spaced-apart position to an approximated position to grasp tissue therebetween.

In another aspect of the present disclosure, a knife is slidably disposed within the shaft and wherein the second function includes deploying the knife between the first and second jaw members to cut tissue grasped therebetween.

In still another aspect of the present disclosure, the function includes supply energy from the first and second jaw members to tissue to treat tissue grasped therebetween.

In yet another aspect of the present disclosure, the control module is subject to one or more override protocols inhibiting actuation of the second actuation assembly prior to actuation of the first actuation assembly, even if the second actuation pattern is input on the sensor surface(s).

In still another aspect of the present disclosure, a first sensor surface and a second sensor surface are provided. The first and second sensor surfaces occupy different portions of the surface area of the housing and are configured to receive input for actuating the first and second actuation assemblies, respectively.

BRIEF DESCRIPTION OF THE DRAWINGS

Various aspects and features of the present disclosure are described herein with reference to the drawings wherein.

DETAILED DESCRIPTION

Figure 1:
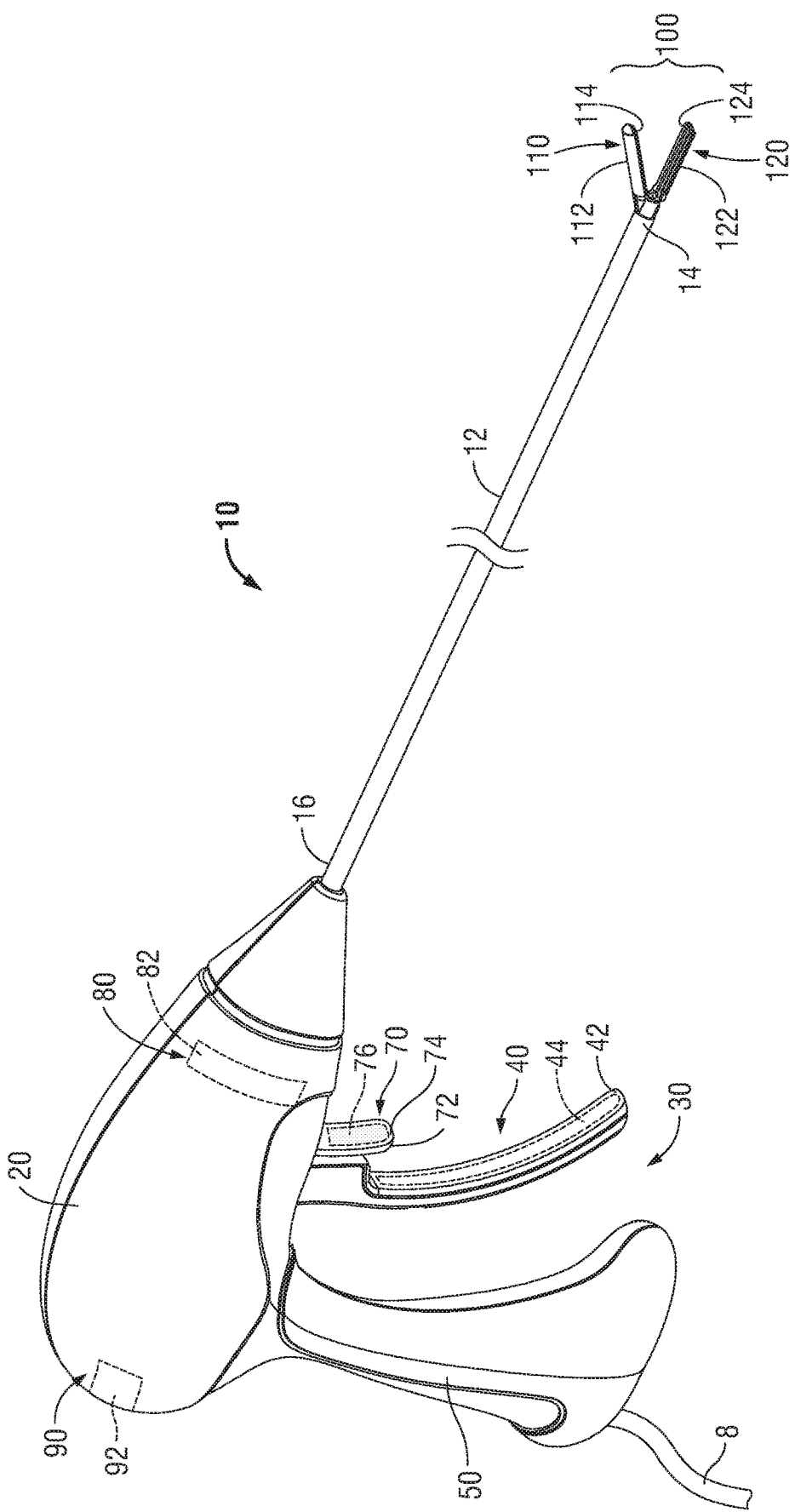
FIG. 1 is a perspective view of a surgical instrument provided in accordance with the present disclosure.

Turning to FIG. 1, a surgical instrument configured for use in accordance with the present disclosure is shown generally identified by reference numeral 10. Surgical instrument 10 is illustrated and described herein as an electrosurgical forceps 10 configured for use in connection with endoscopic surgical procedures for grasping, treating, and/or dividing tissue. However, the aspects and features of the present disclosure are equally applicable for use with any other suitable surgical instrument. Obviously, different electrical and mechanical connections and considerations apply to each particular type of instrument; however, the aspects and features of the present disclosure remain generally consistent regardless of the particular instrument used. For the purposes herein, instrument 10 is generally described.

Referring to FIGS. 1-4, instrument 10 includes a housing 20, a handle assembly 30 operably associated with a jaw actuation assembly 140, a trigger assembly 70 operably associated with a knife actuation assembly 170, a rotating assembly 80 operably associated with a rotation actuation assembly 180, an energy activation assembly 90 operably associated with a generator or other source of energy (not shown), and an end effector assembly 100. Instrument 10 further includes a shaft 12 having a distal end 14 configured to mechanically engage end effector assembly 100 and a proximal end 16 extending into and operably engaged with rotating assembly 80 within housing 20 (see FIG. 2). A cable 8 is configured to connect instrument 10 to a generator or other source of energy (not shown), although instrument 10 may alternatively be configured to wirelessly couple to the generator or other source of energy (not shown) or may be configured as a hand-held device having power and/or generator components (not shown) disposed on or within housing 20.

Handle assembly 30 includes a grasping handle 50 and an actuation handle 40. Grasping handle 50 is integrally associated with housing 20 and is ergonomically configured for grasping by a surgeon in the palm of the surgeon's hand between the thumb and fingers. Actuation handle 40 is spaced-apart from grasping handle 50 and is fixed relative to housing 20, e.g., integral therewith or otherwise fixedly engaged thereto. Actuation handle 40 defines a distal face 42 configured to support some or all of the surgeon's fingers. Sensor surface 44 of actuation handle 40 is disposed on at least a portion of distal face 42. As detailed below, sensor surface 44 is operably associated with a touch sensor 210 configured to sense pressure application to and/or movement along sensor surface 44.

Touch sensor 210 is configured, based upon the pressure application and/or movement detected, to communicate with control module 130 which, in turn, actuates jaw actuation assembly 140 to impart movement of jaw members 110, 120 of end effector assembly 100 between a spaced-apart position (FIG. 3A) and an approximated position (FIG. 3B) to grasp tissue therebetween. Jaw actuation assembly 140 includes a motor 142, a gear mechanism 144, and a drive bar 150. Motor 142 is coupled, at an input thereof, to control module 130 and is configured to receive power and/or control signals therefrom. Motor 142 is further coupled, at an output thereof, to axle 145 of gear mechanism 144 such that, when activated, motor 142 drives axle 145 to rotate. Axle 145 includes a circular gear member 146 of gear mechanism 144 fixedly mounted thereon. Circular gear member 146 is disposed in meshed engagement with a cylindrical threaded member 147 such that rotation of axle 145 rotates circular gear member 146 to, in turn, effect rotation and longitudinal translation of cylindrical threaded member 147. The proximal end of drive bar 150 is longitudinally fixed but rotatable relative to cylindrical threaded member 147 such that rotation and longitudinal translation of cylindrical threaded member 147 translates drive bar 150 through and relative to housing 20 and shaft 12. The distal end 154 of drive bar 150 is operably coupled to one or both of jaw members 110, 120 of end effector assembly 100 such that longitudinal translation of drive bar 150 through and relative to housing 20 and shaft 12 pivots one or both of jaw members 110, 120 relative to the other from a spaced-apart position (FIG. 3A) to an approximated position (FIG. 3B) to grasp tissue therebetween.

Continuing with reference to FIGS. 1-4, trigger assembly 70 includes a trigger 72 fixed relative to housing 20, e.g., integral therewith or otherwise fixedly engaged thereto, and extending from housing 20 adjacent actuation handle 40. Trigger 72 defines a distal face 74 configured to support a surgeon's finger, e.g., the index finger. Sensor surface 76 of trigger 72 is disposed on at least a portion of distal face 74. As detailed below, sensor surface 76 is operably associated with a touch sensor 220 configured to sense pressure application to and/or movement along sensor surface 76.

Touch sensor 220 is configured, based upon the pressure application and/or movement detected, to communicate with control module 130 which, in turn, actuates knife actuation assembly 170 to deploy knife 171 of end effector assembly 100 from a retracted position (FIG. 3A) to an extended position (FIG. 3B) to cut tissue grasped between jaw members 110, 120 of end effector assembly 100. Knife actuation assembly 170 includes a motor 172, a gear mechanism 174, and a knife bar 179 and is configured to selectively deploy knife 171 of end effector assembly 100. Motor 172 is coupled, at an input thereof, to control module 130 and is configured to receive power and/or control signals therefrom. Motor 172 is further coupled, at an output thereof, to axle 175 of gear mechanism 174 such that, when activated, motor 172 drives axle 175 to rotate. Axle 175 includes a circular gear member 176 of gear mechanism 174 fixedly mounted thereon. Circular gear member 176 is disposed in meshed engagement with a cylindrical threaded member 177 such that rotation of axle 175 rotates circular gear member 176 to, in turn, effect rotation and longitudinal translation of cylindrical threaded member 177. The proximal end 179a of knife bar 179 is longitudinally fixed but rotatable relative to cylindrical threaded member 177 such that rotation and longitudinal translation of cylindrical threaded member 177 translates knife bar 179 through and relative to housing 20 and shaft 12. The distal end 179b of knife bar 179 engages the proximal end of knife 171 such that longitudinal translation of knife bar 179 through and relative to housing 20 and shaft 12 deploys knife 171 from a retracted position (FIG. 3A) to an extended position (FIG. 3B) to cut tissue grasped between jaw members 110, 120.

Rotating assembly 80 includes a sensor surface 82 disposed on housing 20 adjacent actuation handle 40 and trigger 72 and positioned to enable operable contact therewith by a finger, e.g., the index finger, of a surgeon grasping instrument 10, although other positionings of sensor surface 82 are also contemplated. As detailed below, sensor surface 82 is operably associated with a touch sensor 230 configured to sense pressure application to and/or movement along sensor surface 82.

Touch sensor 230 is configured, based upon the pressure application and/or movement detected, to communicate with control module 130 which, in turn, actuates rotation actuation assembly 180 to rotate shaft 12 and, thus, end effector assembly 100 relative to housing 20. Rotation actuation assembly 180 includes a motor 182 and a gear mechanism 184. Motor 182 is coupled, at an input thereof, to control module 130 and is configured to receive power and/or control signals therefrom. Motor 182 is further coupled, at an output thereof, to axle 185 of gear mechanism 184 such that, when activated, motor 182 drives axle 185 to rotate about a vertical axis. Axle 185 includes a circular gear member 186 of gear mechanism 184 fixedly mounted thereon. Circular gear member 186 is disposed in meshed engagement with a cylindrical threaded member 187 such that rotation of axle 185 rotates circular gear member 186 about the vertical axis to, in turn, rotate cylindrical threaded member 187 about a longitudinal axis of shaft 12. The proximal end 16 of shaft 12 is fixedly engaged with cylindrical threaded member 187 such that rotation of cylindrical threaded member 187 rotates shaft 12 about is longitudinal axis relative to housing 20. End effector assembly 100 is engaged at the distal end 14 of shaft 12 such that rotation of shaft 12 effects corresponding rotation of end effector assembly 100 relative to housing 20.

Referring still to FIGS. 1-4, energy activation assembly 90 includes a sensor surface 92 disposed on the rear proximal end of housing 20 and positioned to enable operable contact therewith by the thumb of a surgeon grasping instrument 10, although other positionings of sensor surface 92 are also contemplated. As detailed below, sensor surface 92 is operably associated with a touch sensor 240 configured to sense pressure application to and/or movement along sensor surface 92. Based upon the pressure application and/or movement detected, touch sensor 240 communicates with control module 130 which, in turn, initiates the supply of energy from the generator or other energy source (not shown) to jaw members 110, 120 of end effector assembly 100, via wires 194a, 194b, 196a, 196b, to treat tissue grasped therebetween.

Figure 3A:
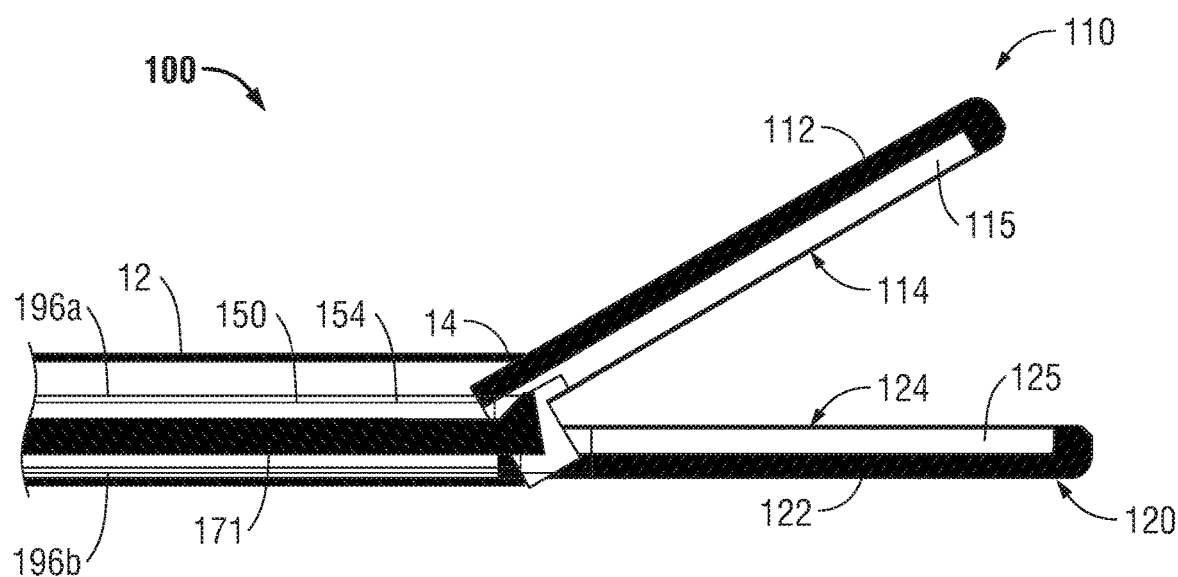
FIG. 3A is an enlarged, side, cross-sectional view of a distal end of the surgical instrument of FIG. 1, wherein jaw members of an end effector assembly of the surgical instrument are disposed in a spaced-apart position and a knife of the end effector assembly of the surgical instrument is disposed in a retracted position.
Figure 3B:
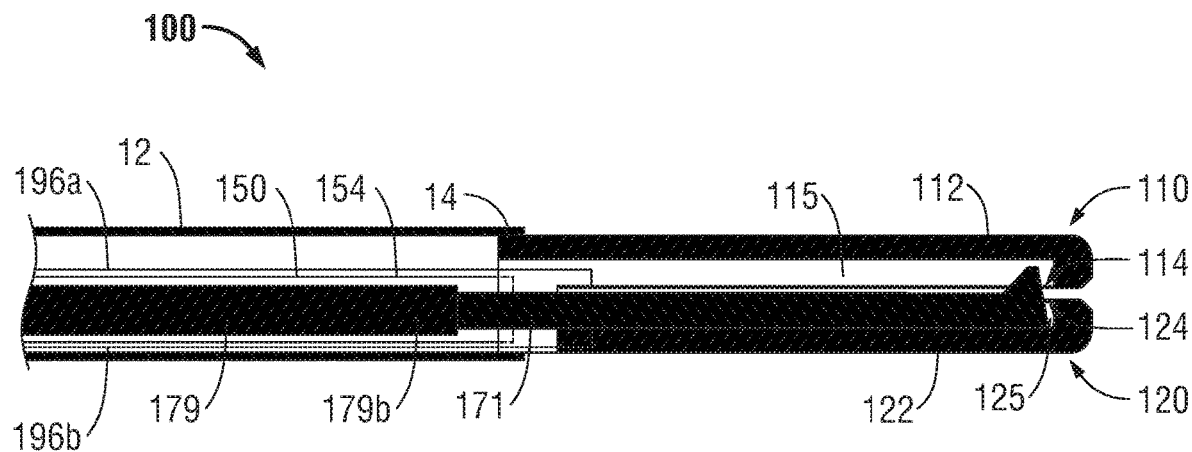
FIG. 3B is an enlarged, side, cross-sectional view of the distal end of the surgical instrument of FIG. 1, wherein the jaw members are disposed in an approximated position and the knife is disposed in an extended position.

Referring in particular to FIGS. 3A and 3B, end effector assembly 100 includes a pair of jaw members 110, 120, each having an outer insulative jaw housing 112, 122 and a tissue-contacting plate 114, 124, respectively. One or both of jaw members 110, 120 is pivotable relative to the other between the spaced-apart position (FIG. 3A) and the approximated position (FIG. 3B) for grasping tissue therebetween. As noted above, one or both of jaw members 110, 120 is coupled to drive bar 150 to enable selective movement of jaw members 110, 120 between the spaced-apart and approximated positions.

Figure 2:
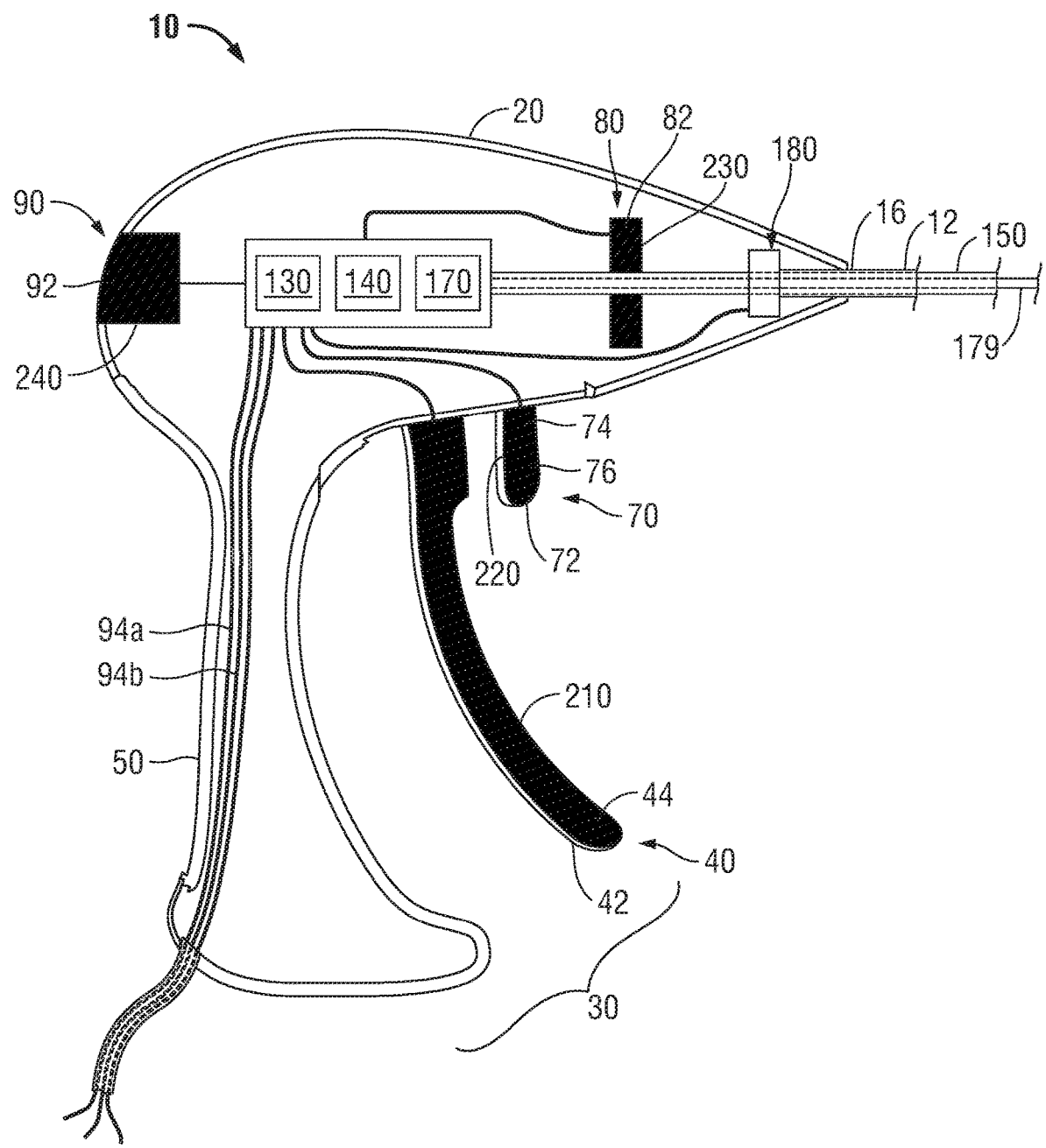
FIG. 2 is an enlarged, perspective, schematic view of a proximal end of the surgical instrument of FIG. 1, wherein a portion of the housing of the surgical instrument has been removed to illustrate the internal components thereof.

Tissue-contacting plates 114, 124 of jaw members 110, 120 of end effector assembly 100 are formed from an electrically-conductive material and are coupled to respective wires 196a, 164b of energy activation assembly 90 extending through housing 20 and shaft 12 (see FIG. 2). More specifically, wires 196a, 196b couple plates 114, 124 to wires 194a, 194b, respectively, which, in turn, are coupled to opposite terminals, e.g., positive (+) and negative (−) terminals, associated with the generator or other energy source (not shown). Thus, bipolar energy may be conducted through tissue grasped between plates 114, 124 to treat tissue. Alternatively, end effector assembly 100 may be configured for delivering monopolar energy to tissue for use in connection with a return pad (not shown) remotely positioned on the patient. Other forms of energy, e.g., ultrasonic, microwave, thermal, light, etc. may additionally or alternatively be used to facilitate tissue treatment. One or both tissue-contacting plates 114, 124 may further include a knife channel 115, 125 defined therein. Knife channels 115, 125 are configured to receive a portion of knife 171 therethrough as knife 171 is deployed to the extended position between jaw members 110, 120.

Referring again to FIGS. 1-4, as noted above, touch sensors 210, 220, 230, 240 are operably associated with respective sensor surfaces 44, 76, 82, 92 such that, together with control module 130, touch sensors 210, 220, 230, 240 enable selective actuation of jaw actuation assembly 140, knife actuation assembly 170, rotation actuation assembly 180, and energy activation assembly 90, respectively. Touch sensors 210, 220, 230, 240 are configured as capacitive sensors, or other suitable sensors configured to sense application of pressure to respective sensor surfaces 44, 76, 82, 92, track movement of pressure application across sensor surfaces 44, 76, 82, 92, track relative movement between two different pressure applications on sensor surfaces 44, 76, 82, 92, etc. Sensors for these purposes are currently employed in consumer electronics, e.g., smart phones, tablets, touch-screen displays, etc.

Each touch sensor 210, 220, 230, 240 has a particular pressure pattern or patterns associated therewith for actuating the particular component thereof, e.g., jaw actuation assembly 140, knife actuation assembly 170, rotation actuation assembly 180, and energy activation assembly 90, respectively. Control module 130 includes a controller 132 and a storage device 138. Storage device 138 of control module 130 may include any suitable component(s) operable for storing information such as, for example, a magnetic disk, flash memory, optical disk, or other suitable data storage device. More specifically, storage device 138 stores information corresponding to the particular pressure pattern or patterns associated with each touch sensor 210, 220, 230, 240 that enables actuation of the corresponding assembly, e.g., jaw actuation assembly 140, knife actuation assembly 170, rotation actuation assembly 180, and energy activation assembly 90, respectively.

Controller 132 of control module 130 includes a processor 134 and a memory 136 and is operably coupled between touch sensors 210, 220, 230, 240 and the corresponding assembly, e.g., jaw actuation assembly 140, knife actuation assembly 170, rotation actuation assembly 180, and energy activation assembly 90, respectively. Controller 132 is further coupled between the wires 194a, 194b, of cable 8, which connect to the generator or other source of energy (not shown) and wires 196a, 196b, which connect to plates 114, 124 of jaw members 110, 120, respectively, of end effector assembly 100. Processor 134 of controller 132 is configured to receive the pressure pattern sensed by touch sensors 210, 220, 230, 240 and to determine whether the pressure pattern corresponds to the actuation pattern of that particular touch sensor 210, 220, 230, 240. This may be accomplished by accessing storage device 138 and comparing the data stored therein indicating the actuation pattern or patterns for a particular touch sensor 210, 220, 230, 240 with the sensed data received from the touch sensor 210, 220, 230, 240. Memory 136 of controller 132 may include any computer memory, e.g., RAM or ROM, mass storage media, removable storage media, combinations thereof, or any other suitable computer-readable storage medium, storing instructions for causing processor 134 to execute particular functions, e.g., to access the data stored in storage device 138 and determine whether or not the particular pressure pattern or patterns have been input.

With respect to surgical instrument 10, sensor surfaces 44, 76, 82, 92 of touch sensors 210, 220, 230, 240, respectively, are positioned to mimic the positioning of traditional mechanical actuators. Further, the particular pressure patterns that enable actuation of jaw actuation assembly 140, knife actuation assembly 170, rotation actuation assembly 180, and energy activation assembly 90, respectively, may likewise be configured to mimic the actuation of traditional mechanical actuators. More specifically, sensor surface 44 is oriented on distal face 42 of actuation handle 40, which is positioned similarly to where a movable handle in a traditional endoscopic surgical forceps may be positioned. The actuation pattern associated with sensor surface 44 and touch sensor 210 may be, for example, pressure contact at four (4) spaced-apart positions on sensor surface 44. Such a configuration mimic's a surgeon pulling a movable handle towards grasping handle 50 with four fingers wrapped around the movable handle. When this pattern is sensed by touch sensor 210 and relayed to control module 130, processor 134 determines that the actuation pattern has been input and, as a result, provides power and control signals to motor 142 of jaw actuation assembly 140 so as to translate drive bar 150, thereby moving jaw members 110, 120 from the spaced-apart position to the approximated position to grasp tissue therebetween. Alternatively, other suitable actuation patterns may be provided. In order to return jaw members 110, 120 back to the spaced-apart position, a second actuation pattern may be input to sensor surface 44.

Sensor surface 76 is oriented on distal face 74 of trigger 72, which is positioned similarly to where a trigger in a traditional endoscopic surgical forceps may be positioned. The actuation pattern associated with sensor surface 76 and touch sensor 220 may be, for example, pressure contact anywhere on sensor surface 76. Such a configuration mimic's a surgeon pulling a trigger proximally with a finger pressed against the trigger. When this pattern is sensed by touch sensor 220 and relayed to control module 130, processor 134 determines that the actuation pattern has been input and, as a result, provides power and control signals to motor 172 of knife actuation assembly 170 so as to translate knife bar 179 distally, thereby moving knife 171 from the retracted position to the extended position to cut tissue grasped between jaw members 110, 120. Alternatively, other suitable actuation patterns may be provided. Further, knife 171 may be returned automatically after deployment, or may be returned upon a second actuation pattern input to sensor surface 76.

Sensor surface 82 is oriented on housing 20 and is positioned similarly to where a rotation wheel in a traditional endoscopic surgical forceps may be positioned. The actuation pattern associated with sensor surface 82 and touch sensor 230 may be, for example, vertical swiping up or down sensor surface 82. Such a configuration mimic's a surgeon rotating a rotation wheel. When this pattern is sensed by touch sensor 230 and relayed to control module 130, processor 134 determines that the actuation pattern has been input and, as a result, provides power and control signals to motor 182 of rotation actuation assembly 180 so as to rotate shaft 12 about its longitudinal axis and relative to housing 20, thereby rotating end effector assembly 100 relative to housing 20. The direction of rotation of shaft 12 and end effector assembly 100 may depend upon the direction of swiping sensor surface 82. Alternatively, other suitable actuation patterns may be provided.

Sensor surface 92 is disposed on housing 20 similarly to where an activation button in a traditional endoscopic surgical forceps may be positioned. The actuation pattern associated with sensor surface 92 and touch sensor 240 may be, for example, applying and maintaining pressure against sensor surface 92. Such a configuration mimic's a surgeon holding down an activation button. When this pattern is sensed by touch sensor 240 and relayed to control module 130, processor 134 determines that the actuation pattern has been input and, as a result, enables the flow of energy from wires 194a, 194b (which are coupled to the generator or other energy source (not shown)) to respective wires 196a, 196b (which are ultimately coupled to plates 114, 124 of jaw members 110, 120) so as to enable conduction of energy between plates 114, 124 of jaw members 110, 120 to treat tissue grasped therebetween. Alternatively, other suitable actuation patterns may be provided. Energy delivery may continue, for example, until pressure is removed from sensor surface 92, or until tissue treatment is complete.

Where surgical instrument 10 includes different energy modalities, e.g., bipolar RF, monopolar RF, ultrasonic, laser, microwave, etc., and/or different energy-based functions, e.g., tissue sealing, electrical cutting, etc., multiple sensor surfaces 92 may be provided and/or different actuation patterns on a single sensor surface 92 may be utilized to activate the different energy modalities/functions. For example, a single-tap on sensor surface 92 may activate the supply of monopolar energy, while a double-tap on the same sensor surface 92 activates the supply of bipolar energy.

In addition to recognizing the above-detailed activation patterns and effecting a corresponding operation based thereon, control module 130 may further be configured to follow protocols to inhibit some or all operations depending upon what other operations have or have not be performed, and/or based on other conditions of the surgical instrument 10. For example, even if the correct pressure pattern is input on sensor surface 76, control module 130 may inhibit deployment of knife 171 if jaw members 110, 120 are disposed in the spaced-apart position. Similarly, even if the correct pressure pattern is input on sensor surface 92, control module 130 may inhibit energy from being supplied to plates 114, 124 of jaw members 110, 120 when jaw members 110, 120 are disposed in the spaced-apart position. As another example, rotation of shaft 12 and end effector assembly 100 may be inhibited, even if a proper actuation pattern is input on sensor surface 82, if jaw members 110, 120 are disposed in the approximated position. Other suitable override protocols are also contemplated.

Figure 4:
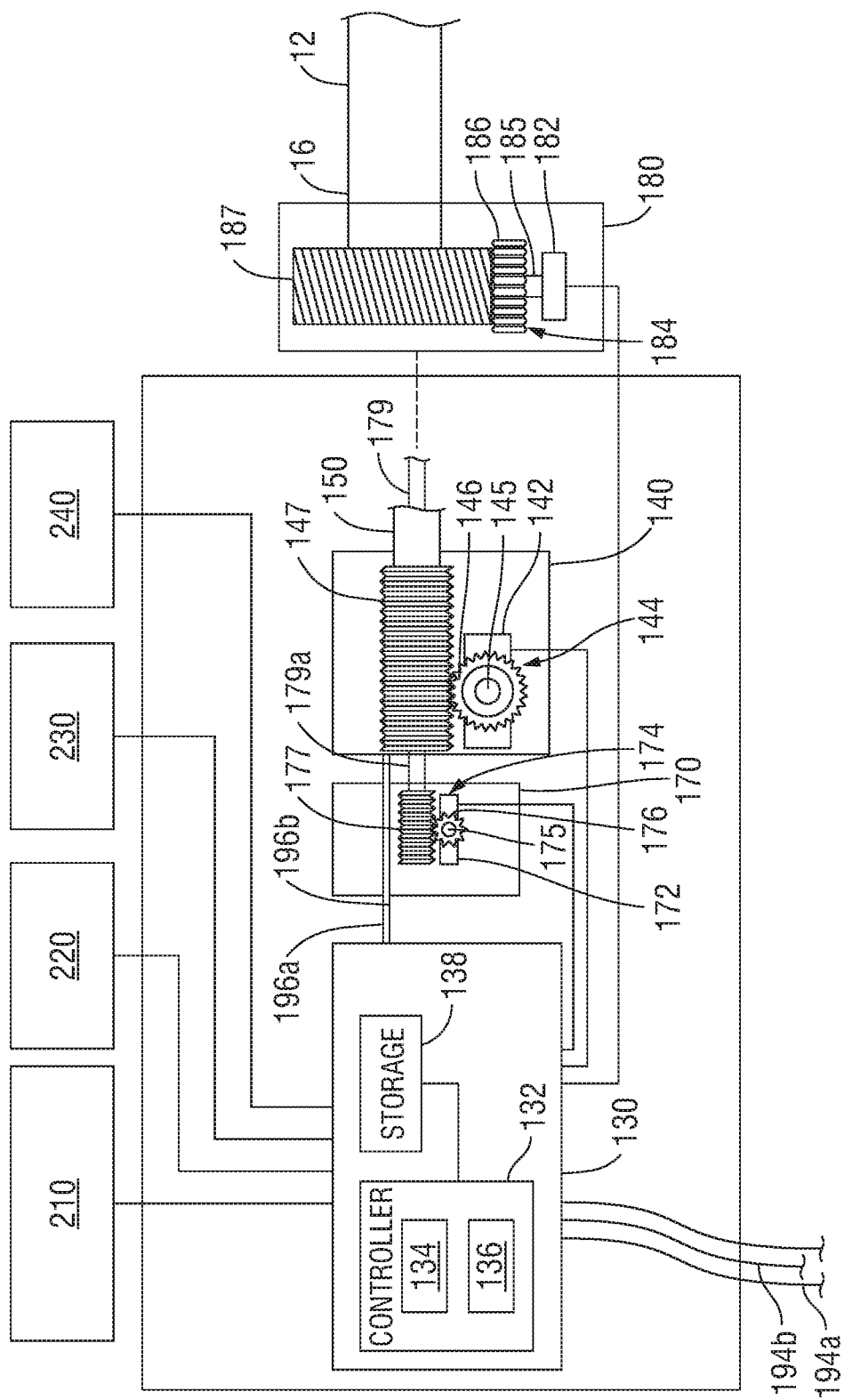
FIG. 4 is a schematic illustration of various actuation assemblies of the surgical instrument of FIG. 1.
Figure 5A:
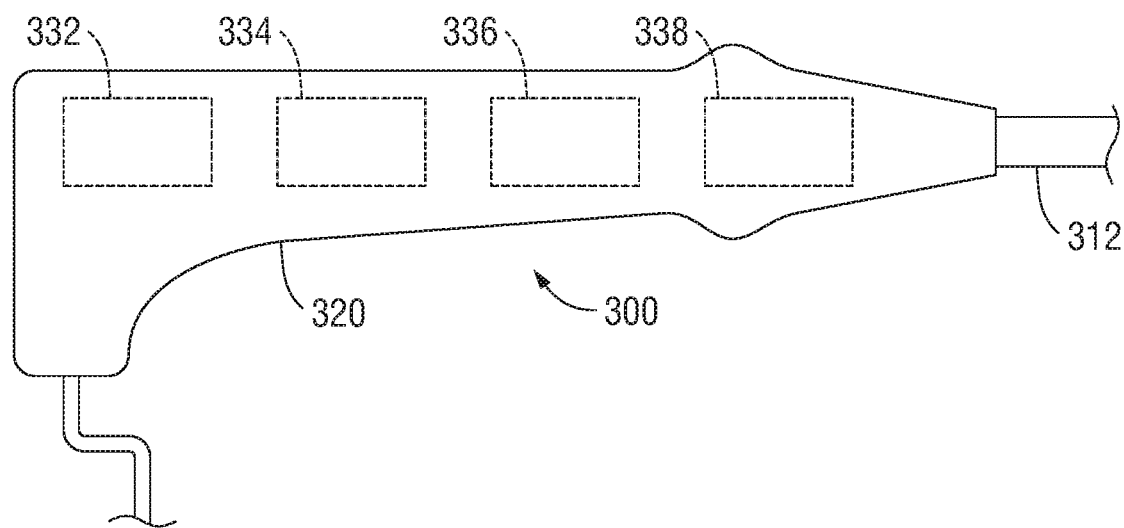
FIG. 5A is a side view of the proximal end of another surgical instrument provided in accordance with the present disclosure.
Figure 5B:
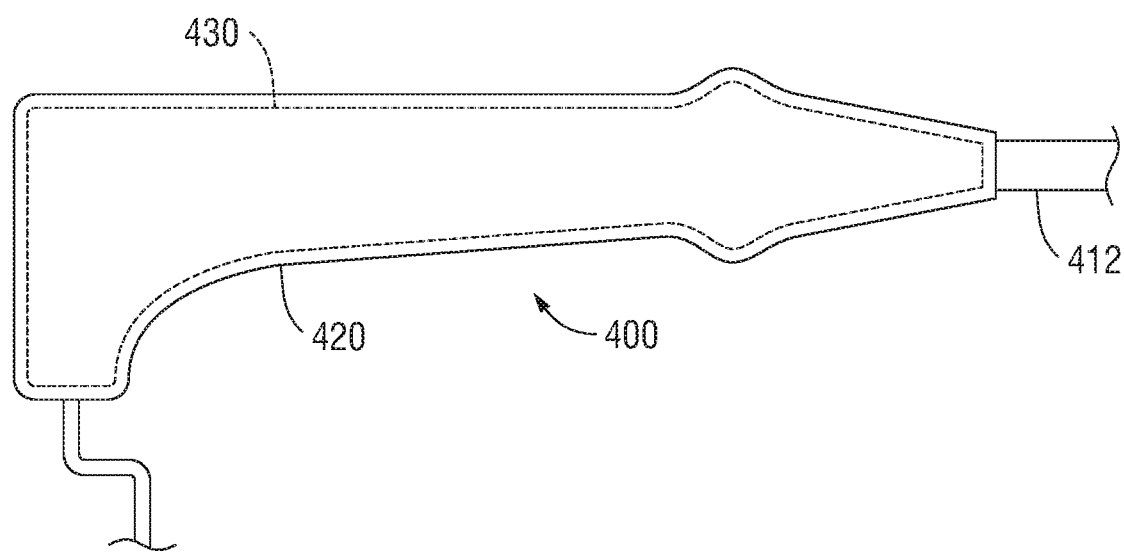
FIG. 5B is a side view of the proximal end of yet another surgical instrument provided in accordance with the present disclosure.

Turning now to FIGS. 5A and 5B, as an alternative to providing a configuration that mimics that of a surgical instrument including traditional mechanical actuators and buttons, other configurations of surgical instruments 300, 400 (FIGS. 5A and 5B, respectively) incorporating the touch actuation features of the present disclosure may be provided. Surgical instruments 300, 400 (FIGS. 5A and 5B, respectively) may include similar internal features as detailed above with respect to instrument 10 (see FIGS. 1 and 4) and, thus, such features will not be detailed below.

Surgical instrument 300, shown in FIG. 5A, includes a housing 320 having a shaft 312 extending distally therefrom. Shaft 312 is configured to support an end effector assembly (not shown), e.g., similar to end effector assembly 100 (FIGS. 3A-3B), at a distal end thereof. Housing 320 may define any suitable configuration that facilitates grasping by a surgeon and access to sensor surfaces 332, 334, 336, 338 disposed thereon.

Continuing with reference to FIG. 5A, sensor surfaces 332, 334, 336, 338 occupy different portions of the surface area of housing 320, each configured to receive input in the form of pressure application and/or movement therealong. Each sensor surface 332, 334, 336, 338 may be configured to receive a particular actuation pattern or patterns associated with a particular function or functions of instrument 300, or some or all sensor surfaces 332, 334, 336, 338 may be configured to receive any or all of the actuation patterns associated with the functions of instrument 300.

Referring to FIG. 5B, instrument 400 is similar to instrument 300 (FIG. 5A) in that instrument 400 includes a housing 420 having a shaft 412 extending distally therefrom. Shaft 412 is configured to support an end effector assembly (not shown), e.g., similar to end effector assembly 100 (FIGS. 3A-3B), at a distal end thereof. Housing 420 may define any suitable configuration that facilitates grasping by a surgeon. Instrument 400 differs from instrument 300 (FIG. 5A) in that, rather than providing a plurality of separate sensor surfaces, instrument 400 includes a continuous sensor surface 430 extending over substantially all of the surface area of housing 420. Thus, a surgeon may input any actuation pattern anywhere on the surface of housing 420 to effect the function associated with the particular actuation pattern input.

Referring to FIGS. 6A-6D, exemplary actuation patterns 610, 620, 630, 640 configured for use with instruments 300, 400 (FIGS. 5A and 5B, respectively) are depicted, although actuation patterns 610, 620, 630, 640 may also be used with instrument 10 (FIG. 1) or any other instrument configured for use in accordance with the aspects and features of the present disclosure. Although exemplary actuation patterns 610, 620, 630, 640 are detailed herein, it is contemplated that any suitable actuation pattern be provided for each particular function.

Figure 6A:
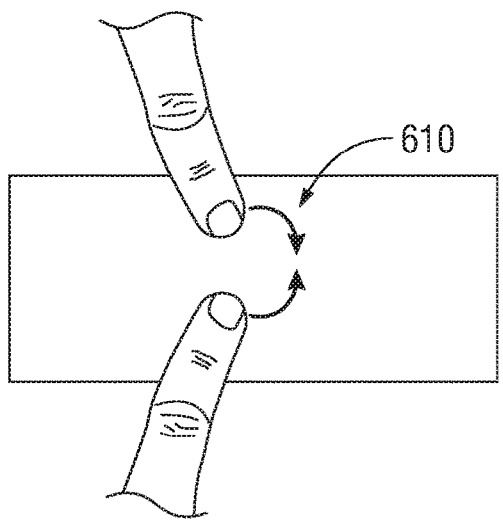
FIG. 6A is a schematic illustration demonstrating an actuation pattern for use with the actuation assemblies of the surgical instruments of FIGS. 1, 5A, and 5B, or any other suitable surgical instrument.

FIG. 6A illustrates an actuation pattern 610 involving pinching adjacent fingers together. Such an actuation pattern 610 may, for example, be suitable for effecting movement of jaw members 110, 120 towards the approximated position (see FIG. 3B) as the action of pinching adjacent fingers together minims the desired movement of jaw members 110, 120 (FIGS. 3A and 3B). Returning jaw members 110, 120 (FIGS. 3A and 3B) towards the spaced-apart position may be effected in the opposite manner, that is, by spreading adjacent fingers apart from one another.

Figure 6B:
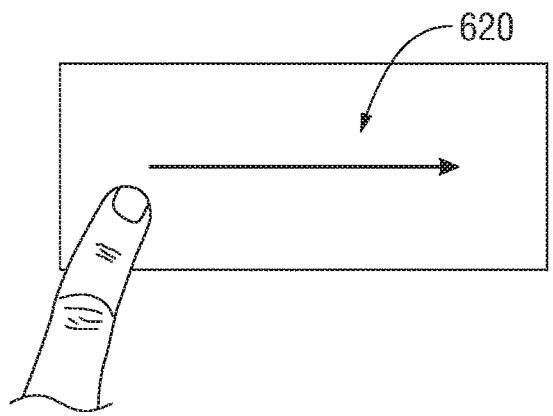
FIG. 6B is another schematic illustration demonstrating an actuation pattern for use with the actuation assemblies of the surgical instruments of FIGS. 1, 5A, and 5B, or any other suitable surgical instrument.

FIG. 6B illustrates an actuation pattern 620 involving translating a finger distally. Such an actuation pattern 620 may, for example, be suitable for deploying knife 171 (FIGS. 3A and 3B). Return of knife 171 (FIGS. 3A and 3B) to the retracted position may be automatically performed after full deployment, or may be effected by translating a finger proximally, opposite of the direction illustrated in FIG. 6B.

Figure 6C:
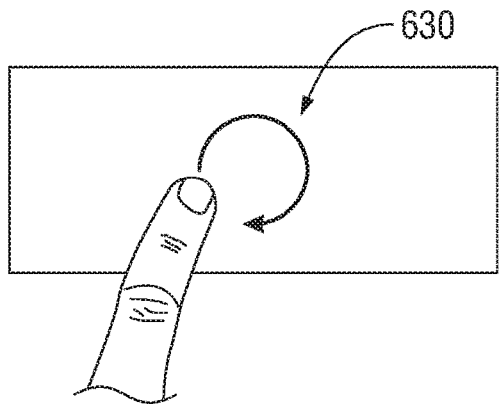
FIG. 6C is yet another schematic illustration demonstrating an actuation pattern for use with the actuation assemblies of the surgical instruments of FIGS. 1, 5A, and 5B, or any other suitable surgical instrument.

FIG. 6C illustrates an actuation pattern 630 involving a finger making a circular motion. Such an actuation pattern 630 may, for example, be suitable for rotating shaft 12 and end effector assembly 100 (see FIG. 1). The direction of the circular motion, e.g., clockwise or counter-clockwise, may determine the direction of rotation of shaft 12 and end effector assembly 100 (see FIG. 1).

Figure 6D:
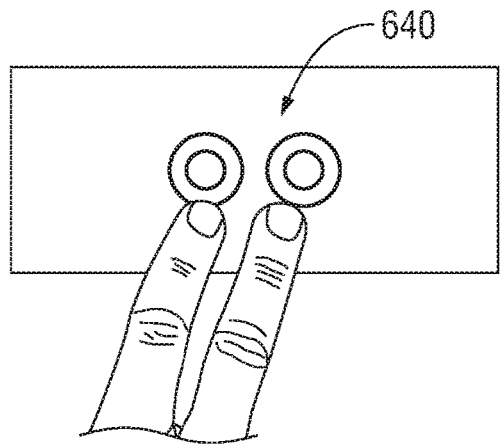
FIG. 6D is still another schematic illustration demonstrating an actuation pattern for use with the actuation assemblies of the surgical instruments of FIGS. 1, 5A, and 5B, or any other suitable surgical instrument.

FIG. 6D illustrates an actuation pattern 640 involving applying simultaneous pressure at two spaced-apart positions in close proximity to one another. Such an actuation pattern 640 may, for example, be suitable for initiating the supply of energy to end effector assembly 100 (FIG. 1). Energy supply may be cut-off upon release of pressure from either or both of the positions, or may continue until tissue treatment is completed. As noted above, different actuation patters may be utilized for different energy modalities and/or to perform different energy-based functions.

Figure 7:
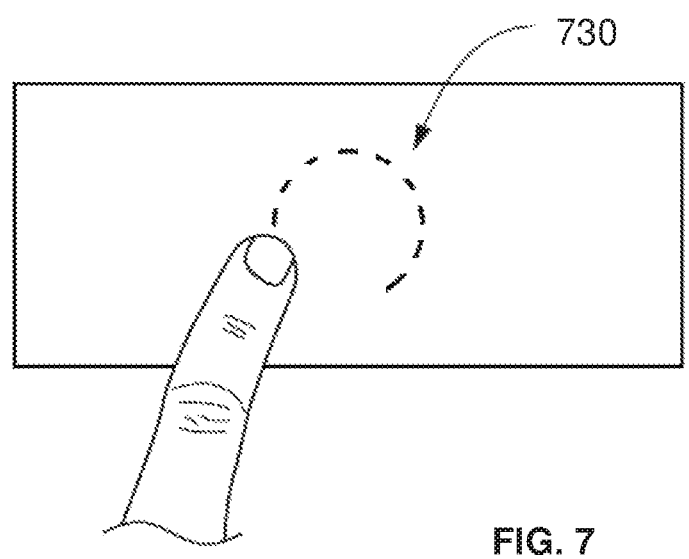
FIG. 7 is a schematic illustration demonstrating use of another touch sensor configured for use with the actuation assemblies of the surgical instruments of FIGS. 1, 5A, and 5B, or any other suitable surgical instrument.

With reference to FIG. 7, a structural guide 730 may be formed on the sensor surface, e.g., on the housing of the surgical instrument, so as to guide a user in inputting the appropriate actuation pattern. More specifically, structural guide 730 provides texture and/or tactile feedback and conforms to the particular actuation pattern to be input into the sensor surface so as to facilitate a user's input of the actuation pattern. For example, as shown in FIG. 7, where the actuation pattern is a semi-circular arc, structural guide 730 may define a semi-circular arc-shaped configuration, allowing a user to trace a finger along structural guide 730 to input the actuation pattern. Structural guide 730 may define different shape configurations, for example, corresponding to any of the actuation patterns detailed above or any other suitable actuation pattern.

Structural guide 730 may be formed as a ridge protruding from the sensor surface, a channel recessed into the sensor surface, a section of different texture (e.g., rougher or smoother) on the sensor surface as compared to the surrounding portions of the sensor surface, or in any other suitable manner so as to facilitate a user's input of the actuation pattern. Further, different structural guides 730 may be provided on the same sensor surface in embodiments where multiple actuation patterns are configured to be received on the same sensor surface.

Referring generally to FIGS. 1-5B, instruments 10, 300, 400 (FIGS. 1, 5A, and 5B, respectively) may be programmable such that the particular actuation pattern associated with each function is definable and/or selectable. For the purposes herein, programming of the instrument will be detailed below with respect to control module 130 of instrument 10 (see FIGS. 1 and 4), although similar programming may be accomplished using the control modules (not shown) of instruments 300 and 400 (FIGS. 5A and 5B, respectively).

Referring to FIG. 4, control module 130 may include a plurality of configuration data files stored in storage device 138. Each configuration data file stores information correlating each function of instrument 10 (FIG. 1) with one or more particular actuation patterns. Accordingly, a surgeon may select a desired configuration data file to be used during operation such that operation of surgical instrument 10 (FIG. 1) is effected via input of the appropriate actuation patterns stored in that configuration data file. As an alternative to pre-set configurations as a whole, the surgeon may select a particular actuation pattern from a plurality of pre-defined actuation patterns for each of the functions of instrument 10 (FIG. 1). Rather than selecting from a plurality of pre-defined actuation patterns, the surgeon may instead input or upload user-defined actuation patterns for storage in storage device 138. Each user-defined actuation pattern may then be assigned to a particular function or functions of instrument 10 (FIG. 1). In addition to defining the particular actuation pattern for a particular function or functions of instrument 10 (FIG. 1), each sensor surface, e.g., sensor surfaces 44, 76, 82, 92 of instrument 10 (FIG. 1) or sensor surfaces 332, 334, 336, 338 of instrument 300 (FIG. 5A), may be dedicated to a particular function, as selected by the surgeon, such that only input of the appropriate actuation pattern on the appropriate sensor surface will perform the corresponding function. The result of the above-detailed customization is a surgical instrument capable of being configured to suit the needs and/or preferences of a particular surgeon.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical instrument, comprising:
   a housing defining a handle and a trigger fixedly disposed thereon, the housing including a first sensor surface of a first sensor disposed on a distal face of the handle, a second sensor surface of a second sensor disposed on a distal face of the trigger, a third sensor surface of a third sensor disposed on a portion of the housing adjacent the handle and the trigger, and a fourth sensor surface of a fourth sensor disposed on a proximal end portion of the housing, the distal faces of the handle and the trigger each having a concave shape and the first and second sensor surfaces contoured to follow the concave shape of the respective distal face of the handle and the trigger, wherein each of the first, second, third, and fourth sensors is configured to sense a respective first, second, third and fourth actuation pattern input on the respective sensor surface mimicking a first, a second, a third, and a fourth actuation motion of first, second, third, and fourth actuation assemblies, respectively, disposed within the housing;
   a shaft extending distally from the housing;
   an end effector disposed at a distal end of the shaft; and
   a control module operably coupled between the first, second, third, and fourth sensor surfaces and the first, second, third, and fourth actuation assemblies, respectively, the control module configured, in response to input of a corresponding actuation pattern on one of the first, second, third, or fourth sensor surfaces, to actuate the corresponding actuation assembly such that a corresponding first, second, third, or fourth function is performed.

2. The surgical instrument according to claim 1, wherein the end effector includes first and second jaw members, and wherein the first function in response to actuation of the first actuation assembly includes moving the first and second jaw members from a spaced-apart position to an approximated position to grasp tissue therebetween.

3. The surgical instrument according to claim 2, wherein the first actuation pattern on the first sensor surface mimics movement of a movable handle to move the first and second jaw members from a spaced-apart position to an approximated position.

4. The surgical instrument according to claim 1, further including a knife slidably disposed within the shaft, and wherein the second function in response to actuation of the second actuation assembly includes deploying the knife relative to the end effector to cut tissue.

5. The surgical instrument according to claim 4, wherein the second actuation pattern on the second sensor surface mimics movement of a trigger to deploy the knife relative to the end effector.

6. The surgical instrument according to claim 1, further including a rotating assembly operably coupled to the end effector, and wherein the third function in response to actuation of the third actuation assembly includes rotating the end effector.

7. The surgical instrument according to claim 1, wherein the third actuation pattern on the third sensor surface mimics movement of a rotation wheel to rotate the end effector.

8. The surgical instrument according to claim 1, further including an energy activation assembly operably coupled to the end effector, and wherein the fourth function in response to actuation of the fourth actuation assembly includes supplying energy from the end effector to tissue to treat tissue.

9. The surgical instrument according to claim 8, wherein the fourth actuation pattern on the fourth sensor surface mimics applying and maintaining pressure on an activation button for supplying energy from the end effector to tissue to treat tissue.

10. The surgical instrument according to claim 1, wherein the control module is subject to at least one override protocol, the at least one override protocol inhibiting actuation of the first, second, third, or fourth actuation assembly even if the actuation pattern is input on the respective sensor surface.

11. The surgical instrument according to claim 1, wherein the actuation pattern is user-programmable.

12. The surgical instrument according to claim 11, wherein the actuation pattern is selected from a plurality of pre-set actuation patterns or user-defined.

13. The surgical instrument according to claim 1, wherein the portion of the housing adjacent the handle and the trigger and the proximal end portion of the housing each has a convex shape, and the third and fourth sensor surfaces are contoured to follow the convex shape of the respective portion and proximal end portion of the housing.

14. The surgical instrument according to claim 1, wherein the handle of the housing is an actuation handle, and the housing further includes a grasping handle, each of the actuation handle, the grasping handle, and trigger fixed relative to the housing.

15. A surgical instrument, comprising:
- a housing including a first sensor having a first sensor surface disposed on the housing, the housing defining a handle fixedly disposed on the housing, the handle including a second sensor having a second sensor surface disposed on the housing, the first and second sensor surfaces contoured to follow a contour of a respective surface of the housing on which the first and second sensor surfaces are disposed, the first sensor configured to sense a first actuation pattern on the first sensor surface and the second sensor configured to sense a second actuation pattern different from the first actuation pattern on the second sensor surface, the first actuation pattern mimicking a first actuation motion of a first actuation assembly of the surgical instrument for performing a first function and the second actuation pattern mimicking a second actuation motion of a second actuation assembly of the surgical instrument for performing a second function, wherein the first sensor does not recognize the second actuation pattern and wherein the second sensor does not recognize the first actuation pattern;
- a shaft extending distally from the housing;
- an end effector disposed at a distal end of the shaft, wherein the first function and the second function are capable of being performed at the end effector;
- the first actuation assembly disposed within the housing and operably coupled to the end effector;
- the second actuation assembly disposed within the housing and operably coupled to the end effector; and
- a control module operably coupled between the first and second sensors and the first and second actuation assemblies, respectively, the control module configured, in response to input of the first actuation pattern on the first sensor surface, to actuate the first actuation assembly such that the first function is performed at the end effector and, in response to input of the second actuation pattern on the second sensor surface, to actuate the second actuation assembly such that the second function is performed at the end effector.

16. The surgical instrument according to claim 15, wherein the end effector includes first and second jaw members, wherein the first function includes moving the first and second jaw members from a spaced-apart position to an approximated position to grasp tissue therebetween, and wherein the first actuation pattern mimics movement of a movable handle to move the first and second jaw members.

17. The surgical instrument according to claim 16, further including a knife slidably disposed within the shaft, wherein the second function includes deploying the knife between the first and second jaw members to cut tissue grasped therebetween, and wherein the second actuation pattern mimics movement of a trigger to deploy the knife.

18. The surgical instrument according to claim 15, wherein the control module is subject to at least one override protocol, the at least one override protocol inhibiting actuation of the second actuation assembly prior to actuation of the first actuation assembly, even if the second actuation pattern is input.

19. The surgical instrument according to claim 15, wherein the first and second sensor surfaces each has a concave or convex shape.

* * * * *